United States Patent [19]

Bauer et al.

[11] 3,944,579
[45] Mar. 16, 1976

[54] 2-AMINO-5-PHENYL-4H-3,5-DIHYDRO-1,5-BENZODIAZEPIN-4-ONES AND SALTS THEREOF

[75] Inventors: Adolf Bauer, Ingelheim am Rhein; Karl Heinz Weber; Klaus Minck, both of Gau-Algesheim; Peter Danneberg, Ingelheim am Rhein, all of Germany

[73] Assignee: Boehringer Ingelheim GmbH, Ingelheim am Rhein, Germany

[22] Filed: July 10, 1974

[21] Appl. No.: 487,221

Related U.S. Application Data

[63] Continuation-in-part of Ser. No. 194,001, Oct. 29, 1971, Pat. No. 3,862,136.

[30] Foreign Application Priority Data

July 11, 1973 United Kingdom............... 33044/73
Oct. 23, 1973 United Kingdom............... 49219/73

[52] U.S. Cl............................ 260/239.3 B; 424/244
[51] Int. Cl.².......................................... C07D 243/12
[58] Field of Search ............................. 260/239.3 B

[56] References Cited
UNITED STATES PATENTS
3,321,468   5/1967   Krapcho et al............... 260/239.3 B OTHER PUBLICATIONS
Buyle et al., "Tetrahedron," Vol. 25, pp. 3453–3459 (1969).
Bauer et al., "J. Med. Chem.," (1973) Vol. 16, No. 9, pp. 1011–1014.

Primary Examiner—Henry R. Jiles
Assistant Examiner—Robert T. Bond
Attorney, Agent, or Firm—Hammond & Littell

[57] ABSTRACT

Compounds of the formula

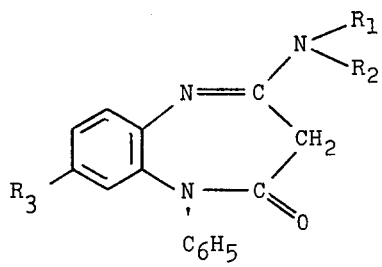

wherein
$R_1$ and $R_2$ are each hydrogen or methyl, and
$R_3$ is chlorine, bromine or nitro, and non-toxic, pharmacologically acceptable acid addition salts thereof; the compounds as well as their salts are useful as tranquilizers.

3 Claims, No Drawings

2-AMINO-5-PHENYL-4H-3,5-DIHYDRO-1,5-BENZODIAZEPIN-4-ONES AND SALTS THEREOF

This is a continuation-in-part of copending application Ser. No. 194,001 filed Oct. 29, 1971, now U.S. Pat. No. 3,862,136.

This invention relates to novel 2-amino-5-phenyl-4H-3,5-dihydro-1,5-benzodiazepin-4-ones and non-toxic, pharmacologically acceptable acid addition salts thereof, as well as to a method of preparing these compounds.

More particularly, the present invention relates to a novel class of compounds represented by the formula

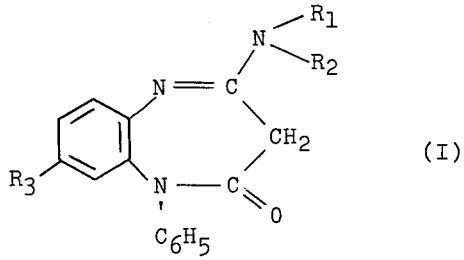

wherein
$R_1$ and $R_2$ are each hydrogen or methyl, and
$R_3$ is chlorine, bromine or nitro, and non-toxic, pharmacologically acceptable acid addition salts thereof.

The compounds embraced by formula I above may be prepared by reacting a compound of the formula

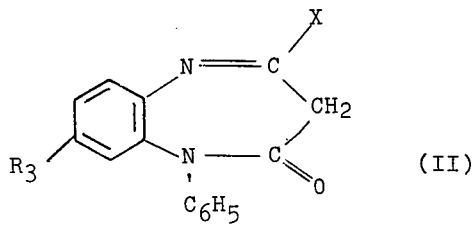

wherein
$R_3$ has the same meanings as in formula I, and
X is halogen, $-OR_4$ or $-SR_4$, where $R_4$ is alkyl of 1 to 4 carbon atoms,
with an amine of the formula

wherein $R_1$ and $R_2$ have the same meanings as in formula I.

More particularly, the reaction is carried out by first dissolving the starting compound of the formula II in an inert organic solvent, such as diethyleneglycol diethyl ether, dioxane or tetrahydrofuran, and either introducing into the solution the gaseous amine or adding to the solution the liquid amine or a solution of the amine of the formula III. Depending upon the particular starting compound, the addition of the amine is carried out while cooling the solution, at room temperature or at a moderately elevated temperature.

A compound of the formula I may also be prepared by reacting the starting compound of the formula II in the above-described manner with ammonia and subsequently methylating or dimethylating the resulting primary amino group in the 2-position by conventional methods with a methylating agent, such as a methyl halide, methyl sulfate or dimethyl sulfate, or by means of the Leuckart-Wallach Reaction [see Berichte 18, 2341 (1885), and Annalen 272, 100 (1892)].

The starting compounds of the formula II are also new; those wherein X is halogen may be prepared by reacting a compound of the formula

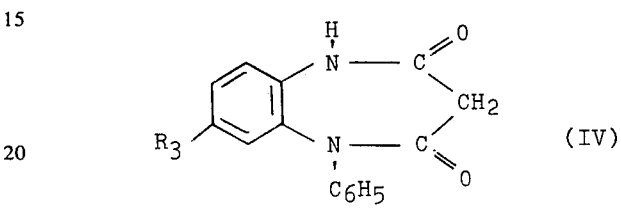

wherein $R_3$ has the same meanings as in formula I, with an inorganic acid halide, preferably a phosphorus pentahalide, in the presence of an anhydrous inert organic solvent, such as dioxane, at a temperature between about $-50°$ and $+50°C$. Those compounds of the formula II wherein X is $-SR_4$ or $-OR_4$, as defined above, may be obtained by selective conversion of the keto-group in the 2-position of the correspondng compound of the formula IV into the thiol group followed by alkylation, or by reacting a compound of the formula IV with the corresponding trialkyloxonium fluoroborate, as described in our U.S. Pat. No. 3,711,467 issued Jan. 16, 1973.

However, a compound of the formula II wherein X is $-OR_4$ or $-SR_4$, as defined above, may also be prepared by reacting a corresponding compound of the formula II wherein X is halogen with a correspondng alkanol or alkylmercaptan, respectively.

If the starting compound in the above process for the preparation of a compound of the formula I is a corresponding compound of the formula II wherein X is halogen, it is not necessary to isolate it from the reaction solution reslting from the reaction between the compound of the formula IV and the phosphorus pentahalide; the reaction with the amine of the formula III may be carried out in this reaction solution containing the imide halide.

The compounds of the formula I are organic bases and therefore form acid addition salts with inorganic or organic acids. Examples of non-toxic, pharmacologically acceptable acid addition salts are those formed with a hydrohalic acid, sulfuric acid, methanesulfonic acid, toluenesulfonic acid, 8-chlorotheophylline or the like.

Specific examples of end products of the formula I or non-toxic acid addition salts thereof which are obtained by the above-described procedures are the following:

2-amino-7-bromo-5-phenyl-4H-3,5-dihydro-1,5-benzodiazepin-4-one,
2-amino-7-chloro-5-phenyl-4H-3,5-dihydro-1,5-benzodiazepin-4-one,
2-amino-7-nitro-5-phenyl-4H-3,5-dihydro-1,5-benzodiazepin-4-one, 7-chloro-2-methylamino-5-phenyl-4H-3,5-dihydro-1,5-benzodiazepin-4-one, 2-methylamino-7-nitro-5-phenyl-4H-3,5-dihydro-1,5-benzodiazepin-4-one, 7-chloro-2-dimethylamino-5-phenyl-4H-3,5-dihydro-1,5-benzodiazepin-4-one, and 2-dimethylamino-7-nitro-5-phenyl-4H-3,5-dihydro-1,5-benzodiazepin-4-one.

The following examples illustrate the present invention and will enable others skilled in the art to understand it more completely. It should be understood, however, that the invention is not limited solely to the particular examples given below.

EXAMPLE 1

2-Amino-7-chloro-5-phenyl-4H-3,5-dihydro-1,5-benzodiazepin-4-one and its hydrochloride A solution of 15 gm of 7-chloro-5-phenyl-4H-3,5-dihydro-1,5-benzodiazepine-2,4-dione in 500 ml of dry diethyleneglycol dimethylether was admixed at 15°C. with 40 gm of phosphorus pentachloride and 0.4 ml of dimethylformamide, and the mixture was allowed to stand for 30 minutes. Thereafter, the reaction solution was poured into a solution of dry ammonia in methanol, the mixed solution was diluted with water and extracted three times with methylene chloride, and the combined extracts were evaporated in vacuo. The residue was dissolved in 60 ml of absolute acetone, the solution was acidified with an excess of ethereal hydrochloric acid, ether was added to the acid solution, and the precipitate formed thereby, the hydrocloride of 2-amino-7-chloro-5-phenyl- 4H-3,5-dihydro-1,5-benzodiazepin-4-one, was collected by vacuum filtration. The filter cake was washed with ether and suspended in water, the aqueous suspension was made alkaline with ammonia and then extracted with ethyl acetate, and the product was crystallized out by addition of ether, yielding 5.8 gm (39% of theory) of the compound of the formula

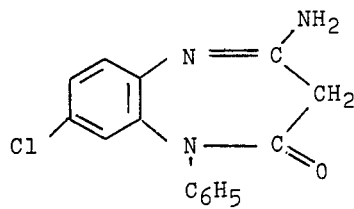

having a melting point of 242°–243°C.

EXAMPLE 2

2-Amino-7-bromo-5-phenyl-4H-3,5-dihydro-1,5-benzodiazepin-4-one, its hydrochloride and its methanesulfonate 13 gm of 7-bromo-5-phenyl-1H-2,3,4,5-tetrahydro-1,5-benzodiazepine-2,4-dione were dissolved in one liter of hot dioxane, the solution was allowed to cool to 15°C., and then, while stirring the solution, 50 gm of phosphorus pentabromide were added thereto. The mixture was allowed to react for 30 minutes, and then, while cooling and stirring, a vigorous stream of dry ammonia was passed therethrough until the resulting suspension reacted alkaline, taking care that the temperature did not rise about 20°C. Subsequently, the suspension was evaporated in vacuo, the residue was admixed with aqueous ammonia, the resulting mixture was extracted several times with methylene chloride, and the combined extracts were washed with water until neutral, dried with magnesium sulfate and evaporated in vacuo. The residue was taken up in acetone, the resulting solution was acidified with ethereal hydrochloric acid, and the precipitate formed thereby, i.e. the hydrochloride of 2-amino-7-bromo-5-phenyl-4H-3,5-dihydro-1,5-benzodiazepin-4-one, was collected by vacuum filtration. The filter cake was washed with ether and suspended in aqueous ammonia, the suspension was extracted with methylene chloride, the extract solution was dried with magnesium sulfate and evaporated, and the residue was recrystallized from isopropyl ether, yielding 8.2 gm (63% of theory) of the compound of the formula

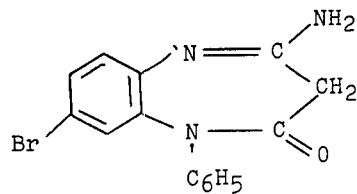

having a melting point of 248°–249°C.

Its methanesulfonate had a melting point of 276°–277.5°C.

EXAMPLE 3

2-Dimethylamino-5-phenyl-7-nitro-4H-3,5-dihydro-1,5-benzodiazepin-4-one 2 gm of 2-amino-5-phenyl-7-nitro-4H-3,5-dihydro-1,5-benzodiazepin-4-one, 5 ml of methyl iodide and 1 gm of sodium methylate were dissolved in 30 ml of dimethylacetamide, and the ensuing exothermic reaction was interrupted after 30 minutes. Thereafter, the reaction solution was evaporated, the residue was taken up in ethyl acetate, and the resulting solution was extracted with water. The organic phase was dried with magnesium sulfate and then evaporated, and the residue was recrystallized from ether, yielding 87% of theory of the compound of the formula

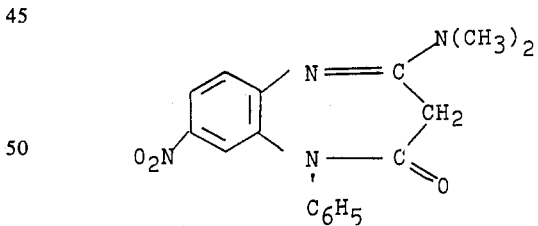

having a melting point of 219°–220°C.

EXAMPLE 4

Using a procedure analogous to that described in Example 1, 2-amino-5-phenyl-7-nitro-4H-3,5-dihydro-1,5-benzodiazepin-4-one, m. p. 219°–220°C., of the formula

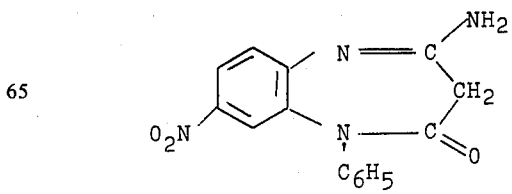

was prepared from 5-phenyl-7-nitro-1H-2,3,4,5-tetrahydro-1,5-benzodiazepine-2,4-dione.

EXAMPLE 5

Using a procedure analogous to that described in Example 1, 2-methylamino-5-phenyl-7-chloro-4H-3,5-dihydro-1,5-benzodiazepin-4-one, m. p. 218°–219°C., of the formula

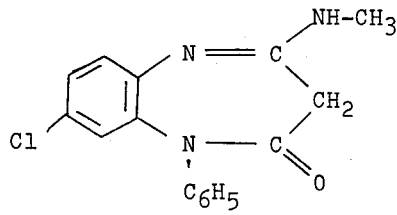

was prepared from 2-ethoxy-5-phenyl-7-chloro-4H-3,5-dihydro-1,5-benzodiazepin-4-one and methylamine.

EXAMPLE 6

Using a procedure analogous to that described in Example 1, 2-dimethylamino-5-phenyl-7-chloro-4H-3,5-dihydro-1,5-benzodiazepin-4-one, m. p. 142°–145°C., of the formula

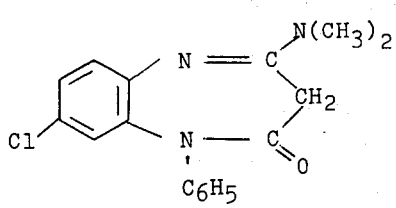

was prepared from 2-amino-5-phenyl-7-chloro-4H-3,5-dihydro-1,5-benzodiazepin-4-one and dimethylacetamide.

EXAMPLE 7

Using a procedure analogous to that described in Example 1, 2-methylamino-5-phenyl-7-nitro-4H-3,5-dihydro-1,5-benzodiazepin-4-one, m. p. 217°–219°C., of the formula

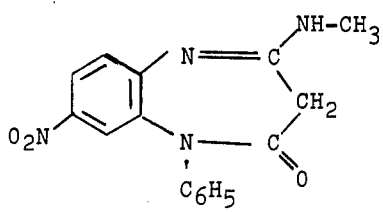

was prepared from 2-ethoxy-5-phenyl-7-nitro-4H-3,5-dihydro-1,5-benzodiazepin-4-one and methylamine.

EXAMPLE 8

Using a procedure analogous to that described in Example 1, 2-amino-5-phenyl-7-nitro-4H-3,5-dihydro-1,5-benzodiazepin-4-one of the formula

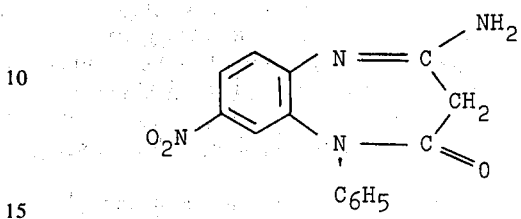

was prepared from 5-phenyl-7-nitro-1H-2,3,4,5-tetrahydro-1,5-benzodiazepin-2,4-dione and ammonia. Its methanesulfonate had a melting point of 238°–239.5°C.

The compounds according to the present invention, that is, those embraced by formula I and their non-toxic, pharmacologically acceptable acid addition salts, have useful pharmacodynamic properties. More particularly, the compounds of the instant invention exhibit tranquilizing activities in warm-blooded animals, such as mice, rats and minks.

In addition, the compounds of the present invention are useful as intermediates for the preparation of other tranquilizers of the benzodiazepine class.

For pharmaceutical purposes the compounds according to the present invention are administered to warm-blooded animals perorally or parenterally as active ingredients in customary pharmaceutical dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective tranquilizing dosage unit of the compounds according to the present invention is from 0.0083 to 0.84 mgm/kg body weight, preferably from 0.0166 to 0.42 mgm/kg, and the preferred daily dose is from 0.083 to 2.5 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 9

Coated Pills

The pill core composition is compounded from the following ingredients:

| | |
|---|---|
| 2-Amino-5-phenyl-7-bromo-4H-3,5-dihydro-1,5-benzodiazepin-4-one . HCl | 5.0 parts |
| Lactose | 28.5 parts |
| Corn starch | 15.0 parts |
| Gelatin | 1.0 parts |
| Magnesium stearate | 0.5 parts |
| Total | 50.0 parts |

Preparation

The benzodiazepinone compound is intimately admixed with the lactose and the corn starch, the mixture is moistened with an aqueous 10% solution of the gelatin, the moist mass is forced through a 1 mm-mesh screen, the resulting granulate is dried at 40°C. and again passed through the screen, the dry granulate is admixed with the magnesium stearate, and the composition is compressed into 50 mgm-pill cores which are subsequently coated in conventional manner with a thin shell consisting essentially of a mixture of sugar, titanium oxide, talcum and gum arabic, and finally polished with beeswax. Each coated pill contains 5 mgm of the benzodiazepinone compound and is an oral dosage unit composition with effective tranquilizing action.

The same result is obtained when an equal amount of one of the following 4H-3,5-dihydro-1,5-benzodiazepin-4-ones is substituted for the benzodiazepinone compound in the above pill core composition:

2-Amino-7-chloro-5-phenyl-4H-3,5-dihydro-1,5-benzodiazepin-4-one; or
2-Amino-7-nitro-5-phenyl-4H-3,5-dihydro-1,5-benzodiazepin-4-one.

EXAMPLE 10

Suppositories

The suppository composition is compounded from the following ingredients:

| | |
|---|---|
| 2-Amino-5-phenyl-7-bromo-4H-3,5-dihydro-1,5-benzodiazepin-4-one | 5.0 parts |
| Suppository base (e.g. cocoa butter) | 1695.0 parts |
| Total | 1700.0 parts |

Preparation

The finely pulverized benzodiazepinone compound is blended with the aid of an immersion homogenizer into the suppository base which had previously been melted and cooled to 40°C. 1700 mgm-portions of the resulting composition are poured at 35°C. into cooled suppository molds and allowed to harden. Each suppository contains 5 mgm of the benzodiazepin-one compound and is a rectal dosage unit composition with effective tranquilizing action.

The same result is obtained when an equal amount of 2-amino-7-nitro-5-phenyl-4H-3,5-dihydro-1,5-benzodiazepin-4-one is substituted for the benzodiazepinone compound in the above suppository composition.

Analogous results are obtained when any one of the other compounds embraced by formula I or a non-toxic acid addition salt thereof is substituted for the particular benzodiazepinone in Examples 9 and 10. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

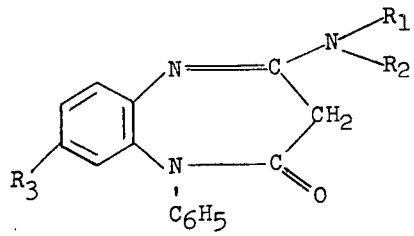

wherein
$R_1$ and $R_2$ are each hydrogen or methyl, and
$R_3$ is chlorine, bromine or nitro, or a non-toxic, pharmacologically acceptable acid addition salt thereof.

2. A compound of claim 1, which is 2-amino-7-bromo-5-phenyl-4H-3,5-dihydro-1,5-benzodiazepin-4-one or a non-toxic, pharmacologically acceptable acid addition salt thereof.

3. A compound of claim 1, which is 2-amino-7-nitro-5-phenyl-4H-1,5-dihydro-1,5-benzodiazepin-4-one or a non-toxic, pharmacologically acceptable acid addition salt thereof.

* * * * *

UNITED STATES PATENT OFFICE
CERTIFICATE OF CORRECTION

Patent No. 3,944,579　　　　　　　　　Dated　March 16, 1976

Inventor(s)　ADOLF BAUER, KARL HEINZ WEBER, KLAUS MINCK and PETER DANNEBERG

It is certified that error appears in the above-identified patent and that said Letters Patent are hereby corrected as shown below:

On the Title Page

Item [30]　　Foreign Application Priority Date - Delete "July 11, 1973, United Kingdom, 33044/73; October 23, 1973, United Kingdom, 49219/73" Insert -- November 2, 1970　Germany P 20 53 680.5 --

Signed and Sealed this

Third Day of August 1976

[SEAL]

Attest:

RUTH C. MASON
*Attesting Officer*

C. MARSHALL DANN
*Commissioner of Patents and Trademarks*